(12) United States Patent
Katase

(10) Patent No.: US 7,131,599 B2
(45) Date of Patent: Nov. 7, 2006

(54) ATOMIZING DEVICE

(75) Inventor: Makoto Katase, Nagano-ken (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 10/915,128

(22) Filed: Aug. 10, 2004

(65) Prior Publication Data

US 2005/0067503 A1  Mar. 31, 2005

(30) Foreign Application Priority Data

Aug. 11, 2003  (JP) .............................. 2003-291632

(51) Int. Cl.
*B05B 1/08* (2006.01)
*A61M 11/06* (2006.01)
*A61M 11/08* (2006.01)
*A61M 11/00* (2006.01)

(52) U.S. Cl. ............................. 239/102.1; 239/102.2; 239/338; 239/350; 128/200.14

(58) Field of Classification Search ............ 239/102.1, 239/102.2, 338, 350, 135, 309, 340, 346, 239/373, 426, 433, 434; 128/200.14, 200.16, 128/200.18, 200.23
See application file for complete search history.

(56) References Cited

U.S. PATENT DOCUMENTS 4,294,407 A * 10/1981 Reichl et al. ............ 239/102.2
4,877,989 A * 10/1989 Drews et al. ........... 310/323.01
5,894,841 A *  4/1999 Voges ..................... 128/203.12
6,062,212 A *  5/2000 Davison et al. ......... 128/200.16
6,196,218 B1*  3/2001 Voges ..................... 128/200.14
6,540,154 B1*  4/2003 Ivri et al. ....................... 239/11
6,629,524 B1* 10/2003 Goodall et al. ......... 128/200.14

FOREIGN PATENT DOCUMENTS

JP          2001-149473         6/2001

* cited by examiner

*Primary Examiner*—Dinh Q. Nguyen
*Assistant Examiner*—Darren Gorman
(74) *Attorney, Agent, or Firm*—Harness, Dickey & Pierce, P.L.C.

(57) ABSTRACT

An atomizing device is provided that comprises: a casing having a release opening; discharging means provided within the casing and having at least one discharge head for discharging a liquid matter as droplets from a nozzle communicating with a cavity by driving an actuator to change a pressure within the cavity filled with the liquid matter; and atomizing means provided within the casing for atomizing the droplets discharged from the discharging means. It is preferred that at least a part of the discharging means and/or at least a part of the atomizing means are detachably mounted to the casing.

10 Claims, 6 Drawing Sheets

ATOMIZING DEVICE

RELATED APPLICATIONS

This application claims priority to Japanese Patent Application No. 2003-291632 filed Aug. 11, 2003 which is hereby expressly incorporated by reference herein in its entirety.

BACKGROUND

1. Technical Field

The present invention relates to an atomizing device.

2. Background Art

One known type of inhalator apparatus for inhaling flavors, medical agents, etc., is a neburizer inhalator equipped with an atomizing device (for example, see Publication of Japanese Patent Application No. 2001-149473).

However, by various types of conventional atomizing devices, the released amount (inhaled amount) of a released matter such as a flavor or a medical agent can not be controlled accurately. Accordingly, the range of application is restricted.

A purpose of the invention is to provide an atomizing device capable of atomizing a liquid matter and controlling the released amount of the atomized liquid matter (released matter) easily and accurately.

SUMMARY

This purpose is achieved by the invention as described below.

An atomizing device of the invention comprises: discharging means having at least one discharge head for discharging a liquid matter as droplets from a nozzle communicating with a cavity by driving an actuator to change the pressure within the cavity filled with the liquid matter; and atomizing means for atomizing the droplets discharged from the discharging means.

By activating the discharging means and the atomizing means, the droplets of the liquid matter are discharged from the discharging means and the droplets are atomized by the atomizing means.

Further, since the fluid jet system (for example, inkjet system) is adopted for the discharging means, the target amount of droplets can be discharged from the discharging means accurately and reliably. Thereby, the liquid matter can be atomized accurately and reliably to the target amount.

An atomizing device of the invention comprises: a casing having a release opening; discharging means provided within the casing and having at least one discharge head for discharging a liquid matter as droplets from a nozzle communicating with a cavity by driving an actuator to change the pressure within the cavity filled with the liquid matter; and atomizing means provided within the casing for atomizing the droplets discharged from the discharging means.

By activating the discharging means and the atomizing means, the droplets of the liquid matter are discharged from the discharging means and the droplets are atomized by the atomizing means.

Further, since the fluid jet system (for example, inkjet system) is adopted for the discharging means, the target amount of droplets can be discharged from the discharging means accurately and reliably. Thereby, the liquid matter can be atomized accurately and reliably to the target amount.

In the atomizing device of the invention, it is preferred that at least a part of the discharging means and/or at least a part of the atomizing means are detachably mounted to the casing.

In this way, the device can be easily cleaned, repaired, or replaced.

In the atomizing device of the invention, it is preferred that the atomizing means comprises heating means for heating and atomizing the droplets discharged from the discharging means.

In this way, the droplets discharged from the discharging means can be atomized easily and reliably.

In the atomizing device of the invention, it is preferred that the atomizing means comprises vibrating means for vibrating and atomizing the droplets discharged from the discharging means.

In this way, the droplets discharged from the discharging means can be atomized easily and reliably.

In the atomizing device of the invention, it is preferred that the atomizing means has a droplet receiving part spaced at a predetermined distance from the nozzle for receiving the droplets.

In this way, the droplets discharged from the discharging means can be atomized easily and reliably.

In the atomizing device of the invention, it is preferred that the atomizing means atomizes the droplets received by the droplet receiving part by heating the droplet receiving part.

In this way, the droplets discharged from the discharging means can be atomized easily and reliably.

In the atomizing device of the invention, it is preferred that the atomizing means atomizes the droplets received by the droplet receiving part by vibrating the droplet receiving part.

In this way, the droplets discharged from the discharging means can be atomized easily and reliably.

In the atomizing device of the invention, it is preferred that the device includes a channel for circulating air between the nozzle and the droplet receiving part, wherein the atomized liquid matter is allowed to flow by the air circulating in the channel.

In this way, the atomized liquid matter can be released smoothly and reliably.

In the atomizing device of the invention, it is preferred that the device includes a mounted portion to which a cartridge having a storage part in which the liquid matter is stored is detachably mounted.

In this way, by attaching the cartridge to the mounted portion of the casing, the liquid matter is supplied from its storage part to the discharging means, and, by detaching the cartridge from the mounted portion of the casing, the supply of the liquid matter from its storage part to the discharging means is stopped.

In the atomizing device of the invention, it is preferred that at least a part of the discharging means and/or at least a part of the atomizing means are provided with the cartridge.

By attaching the cartridge to or detaching it from the mounted portion of the casing, the discharging means and the atomizing means are attached to or detached from the casing integrally with the cartridge.

In the atomizing device of the invention, it is preferred that the device has a power switch for turning ON/OFF a power supply by attaching the cartridge to and detaching it from the mounted portion.

By attaching the cartridge to the mounted portion of the casing, the power supply is turned ON via the power switch, and, by detaching the cartridge from the mounted portion of the casing, the power supply is turned OFF via the power switch.

In the atomizing device of the invention, it is preferred that the liquid matter include a component taken in by a living body.

DETAILED DESCRIPTION

Hereinafter, an electronic inhalator apparatus of the invention will be described according to preferred embodiments shown in the accompanying drawings. Note that in the embodiments as described below the case where an atomizing device of the invention is applied to the electronic inhalator apparatus will be described simply as an example.

Figure 1:
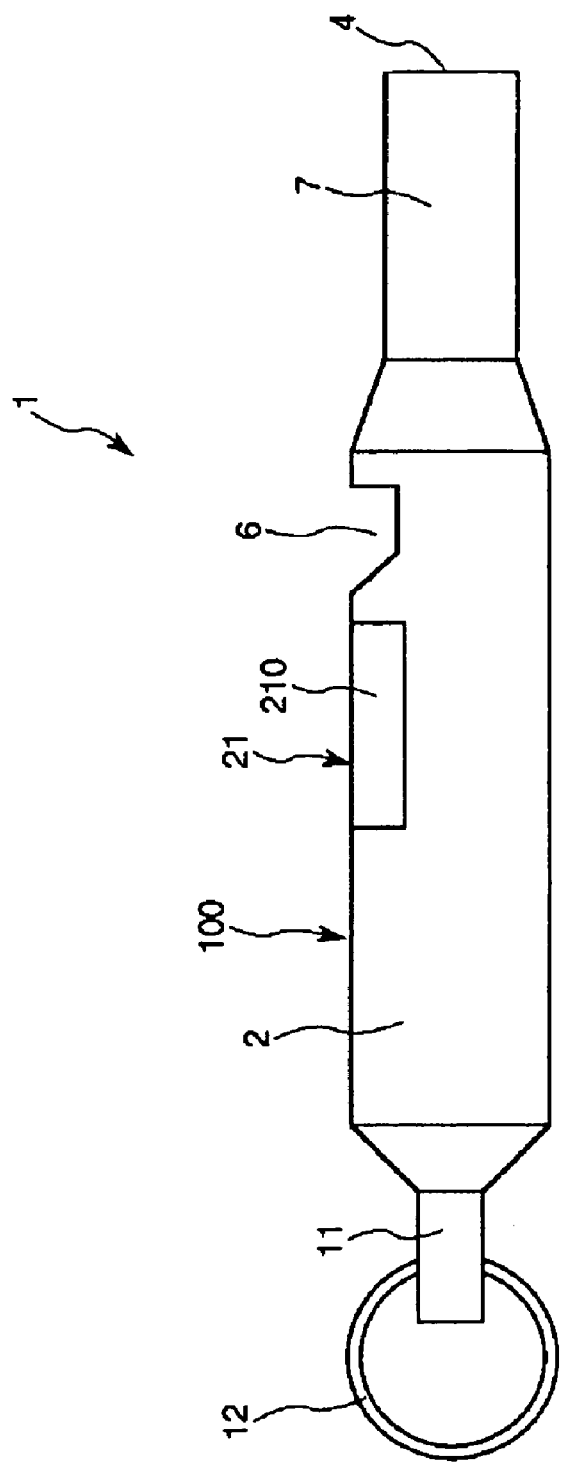
FIG. 1 is a plan view showing the first embodiment in the case where the atomizing device of the invention is applied to the electronic inhalator apparatus.
Figure 2:
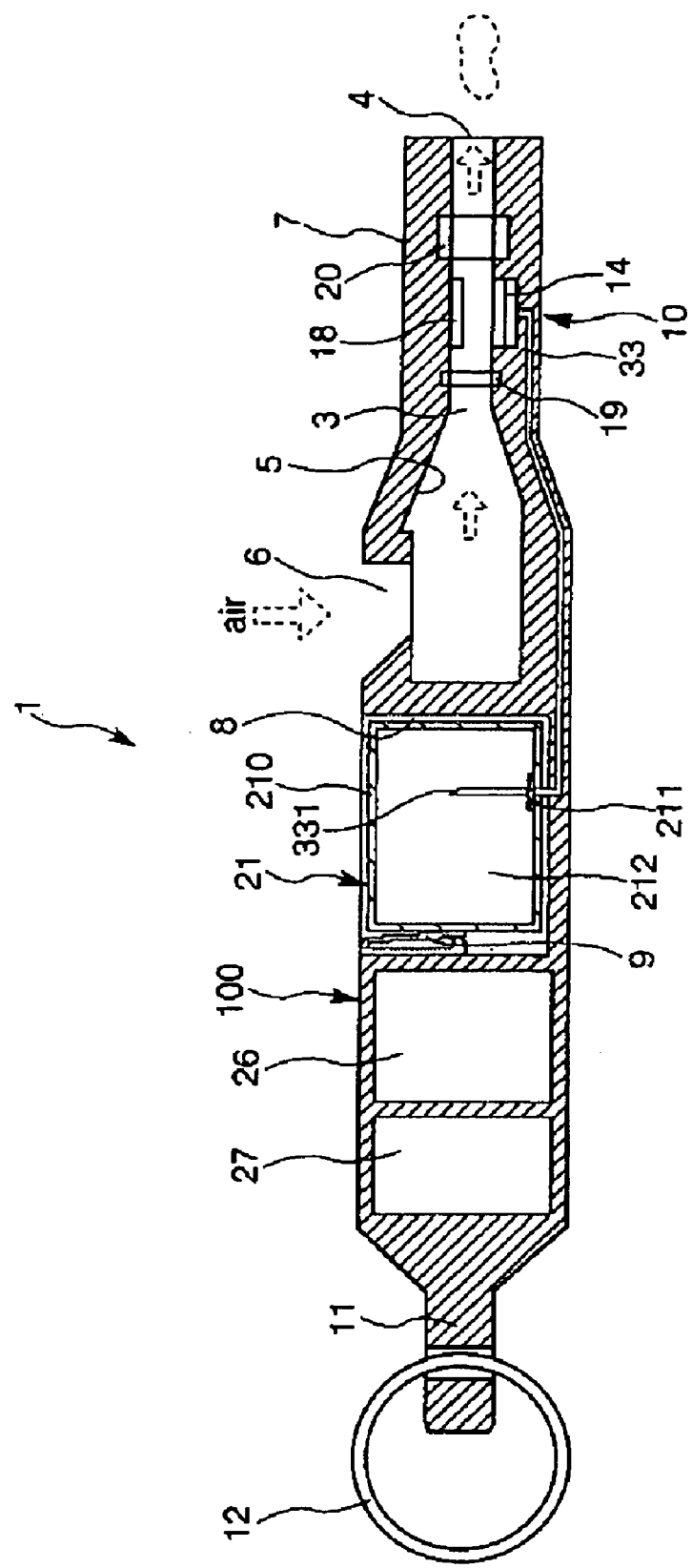
FIG. 2 is a sectional view of FIG. 1.
Figure 3:
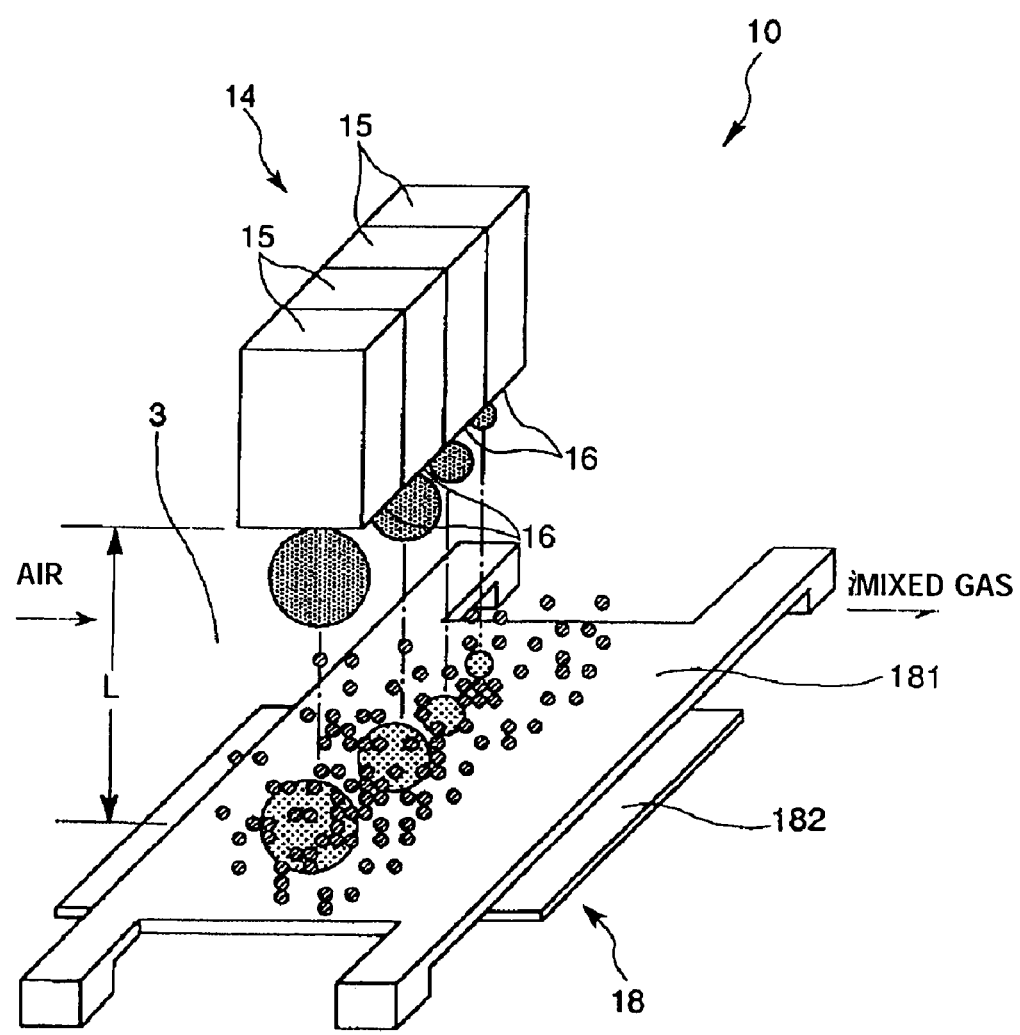
FIG. 3 is a view schematically showing a constitution example of discharge means and atomizing means in FIG. 2
Figure 4:
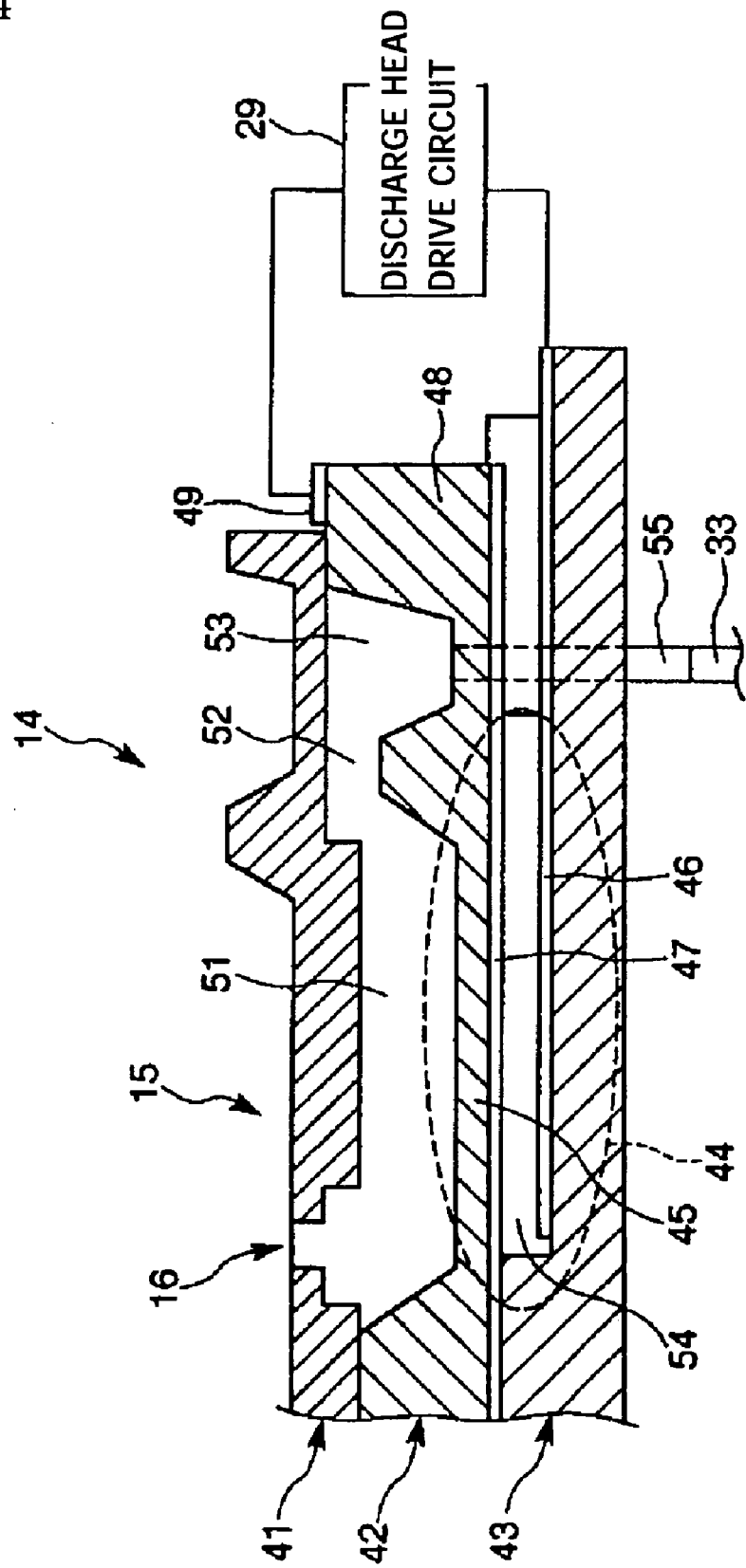
FIG. 4 is a sectional view showing the constitution example of the discharge means.
Figure 5:
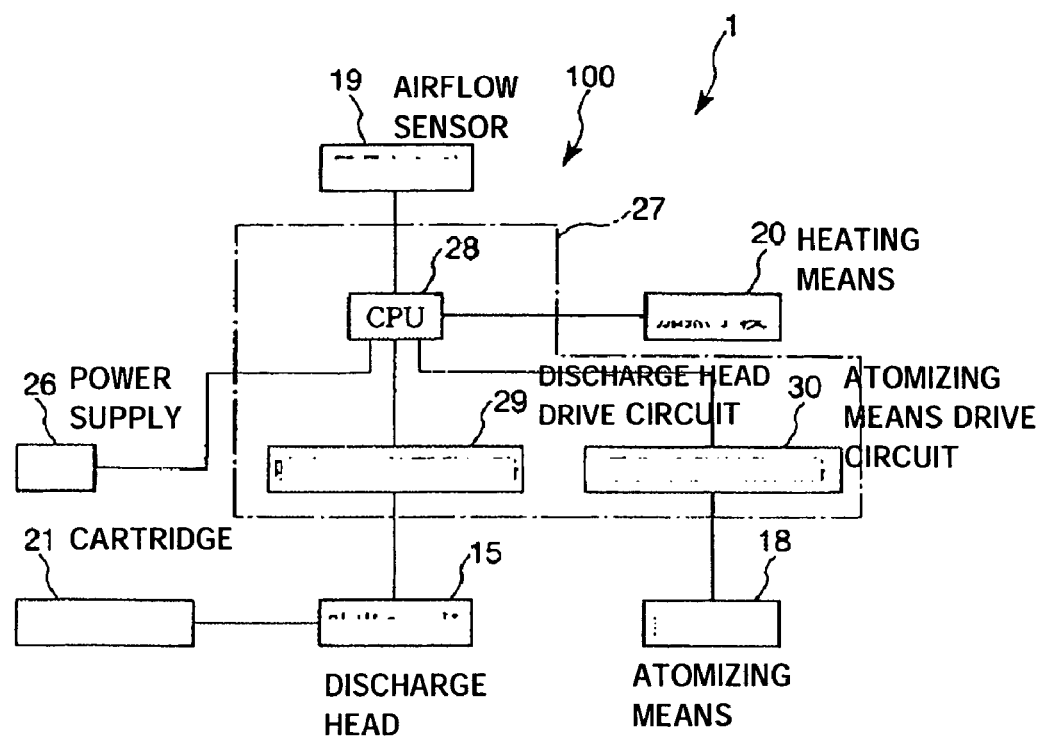
FIG. 5 is a block diagram of the electronic inhalator apparatus of the first embodiment.

In FIGS. 1 to 5, the first embodiment in the case where an atomizing device of the invention is applied to the electronic inhalator apparatus is shown. FIG. 1 is a plan view showing the entire of the electronic inhalator apparatus, FIG. 2 is a sectional view of FIG. 1, FIG. 3 schematically shows a constitution example of discharge means and atomizing means in FIG. 2, FIG. 4 is a sectional view showing the constitution example of the discharge means, and FIG. 5 is a block diagram of the electronic inhalator apparatus.

Note that, for convenience of explanation, the left side in FIGS. 1 and 2 is referred to as a "leading end" and the right side is referred to as a "base end" in the description.

As shown in FIGS. 1 and 2, an electronic inhalator apparatus 1 includes an apparatus main body 100 having an overall form of rod (whistle) shape and a cartridge 21 having a storage part in which a liquid matter including a predetermined component taken in by a living body (hereinafter, also referred to as simply as "liquid matter") is stored.

The apparatus main body 100 includes a casing 2, discharging means 14 for discharging droplets of the liquid matter into the casing 2, atomizing means 18 for atomizing (miniaturizing) the droplets discharged from the discharging means 14, and control means 27 for controlling the drive of the discharging means 14 and the atomizing means 18 etc. The casing 2, discharging means 14, atomizing means 18, and control means 27 constitute a main part of an atomizing device 10.

The overall form of the casing 2 has a rod (whistle) shape. In the base end portion (one end in the longitudinal direction) of the casing 2, a mouthpiece 7 is provided, and, at the center of the mouth piece 7, a channel 3 having a predetermined length for allowing circulation of air, mixed gas of air and a predetermined component, etc. is provided along the longitudinal direction.

The channel 3 has a cross section of a circular shape in the embodiment, and the base end thereof is open (opened) to the end surface center on the base end side of the mouthpiece 7, and the opening portion is formed in an aspiration opening (release opening) 4 for aspiring a predetermined component (mixed gas including air and the predetermined component) into the mouth.

In the middle of the channel 3, a tapered surface 5 having a diameter gradually enlarged toward the leading end is formed, and, on the side nearer the leading end than the tapered surface 5, an intake opening (side opening) 6 penetrating the casing 2 in the radial direction is provided, and the inside of the channel 3 is opened to the outer surface side of the casing 2 via the intake opening 6. While only one intake opening 6 is shown in the embodiment, plural openings may be provided. When breathing with the mouthpiece 7 in the mouth, air is taken into the channel 3 via the intake opening 6, and the air circulates within the channel 3 toward the aspiration opening 4 and flows into the mouth from the aspiration opening 4.

At a part corresponding to the central portion of the channel 3 in the longitudinal direction, the discharging means 14 and the atomizing means 18 are provided so as to face the channel 3, respectively. By the activation of the discharging means 14, droplets of the liquid matter is discharged into the channel 3, and, by the activation of the atomizing means 18, the droplets discharged from the discharging means 14 are atomized (miniaturized), and the atomized liquid matter is mixed with the air circulating within the channel and flows within the channel 3 and flows as mixed gas into the mouth from the aspiration opening 4. The discharging means 14 and atomizing means 18 will be described later, respectively.

The component material of the casing 2 is not limited especially, and, for example, various resins, various metals, various ceramics, etc. can be cited.

Needless to add, the form of the casing 2 and the apparatus main body 100 are not limited to those shown.

The liquid matter is not limited as long as a predetermined component taken in by the living body is included, for example, a solution, a dispersion liquid, an emulsion liquid, etc. can be cited. Further, as the predetermined component, for example, medical components, flavor components, etc. can be cited. By the way, both medical components and flavor components may be included.

The liquid matter including flavor components (flavor generation medium) is a medium that can generate a flavor by being discharged as droplets, and suitably selected according to the application. The flavor generation medium includes, for example, extracted materials from various natural products and a predetermined material of the constituent components thereof. As a flavor material included in the flavor generation medium, for example, in the case where the device is applied as an electronic tobacco (pseudo-smoking instrument), menthol, caffeine, a precursor such as glycoside that generates a flavor by thermal decomposition, and a tobacco component such as tobacco extracted components and tobacco smoke condensed material components and the like can be used. In this case, it is preferred that the flavor generation medium is rendered harmless and the harmful components are eliminated.

Further, the flavor generation medium in the case where the device is applied as an electronic tobacco (pseudo-smoking instrument) can include, for example, a material that produces aerosol when heated, in order to add smoke to the flavor. As the material that produces aerosol, for example, glycerin, polyols such as propylene glycol, lower alcohols, sugars, and a mixture thereof can be used.

Furthermore, to prepare the liquid matter including medical components, a predetermined medical agent is dissolved or dispersed in oil, water, alcohol, or the like, which is harmless to the living body. Thereby, a solution (chemical solution), a dispersion liquid, an emulsion liquid, or the like can be obtained.

By the way, in the case where the atomizing device of the invention is used for another application, the liquid matter is not limited to one including a predetermined component taken in by the living body.

For the discharging means 14, a fluid jet system (for example, inkjet system) is adopted. The fluid jet system is a system for discharging a fluid as droplets from a nozzle communicating with a cavity by driving an actuator to change the pressure within the cavity (pressure chamber) in which the fluid such as liquid and the like is filled. As the fluid jet system, for example, a film boiling fluid jet system such as a thermal jet system (bubble jet system ("bubble jet" is a registered trademark)), a piezoelectric system, an electrostatic system, etc. can be cited. Note that, the invention is not limited to these systems and any system having an equivalent function may be used.

The discharge head of the film boiling fluid jet system such as a thermal jet system (bubble jet system ("bubble jet" is a registered trademark) includes a film boiling type actuator having a heating element (heater) generating heat by being energized. In the film boiling fluid jet system, for example, the heating element generates heat by being energized, and thereby, bubbles are produced and the droplets are discharged by the pressure of the bubbles (change in liquid pressure by the bubbles).

Further, the discharge head of the piezoelectric system has a piezoelectric element and includes a piezoelectric type actuator for utilizing the piezoelectric effect of the piezoelectric element. In the piezoelectric system, for example, a voltage is applied to the piezoelectric element to displace (deform) the piezoelectric element and change the volume of the cavity (pressure chamber), and thereby, the pressure within the cavity 51 is changed to discharge the droplets.

Furthermore, the discharge head of the electrostatic system has an electrostatic type actuator. In the electrostatic system, for example, a coulomb force is generated by applying a voltage between the opposed electrodes of the electrostatic type actuator to displace (deform) the vibrating plate and change the volume of the cavity (pressure chamber), and thereby, the pressure within the cavity 51 is changed to discharge the droplets.

In the embodiment, as shown in FIG. 3, the discharging means 14 includes plural (four in the shown example) discharge heads 15 of the fluid jet system having nozzles 16 for discharging the droplets of the liquid matter. That is, the discharging means 14 includes a head unit having plural discharge heads 15 of the fluid jet system. By the way, the number of discharge heads 15 is not limited to four, but more or less of them may be used.

The respective discharge heads 15 have nozzles 16 formed in different diameters, and, for example, by the combination of ON/OFF of the discharge heads 15, the discharged amount of the liquid matter can be adjusted to the predetermined amount accurately and reliably.

Further, by such adjustment of the discharged amount of the liquid matter, the control of the number of times of activation of the respective discharge heads 15, or the like, the total amount (total discharged amount) of the droplets (liquid matter) discharged from the discharging means 14 can be adjusted (regulated) to the predetermined amount accurately and reliably. That is, the amount of the droplets (liquid matter) discharged from the discharging means 14 can be controlled easily, accurately and reliably.

As described below, as a representative, the example of the discharge head 15 in the case where the electrostatic system is adopted will be described according to FIG. 4. Note that, in FIG. 4, only one of the plural discharge heads 15 is shown.

As shown in FIG. 4, the discharge head 15 has a three-layer structure formed by laminating a nozzle plate 41 made of silicon on the upper side of a silicon substrate 42 and laminating a glass substrate 43 on the lower side thereof.

Between the silicon substrate 42 and the nozzle plate 41, a cavity (pressure chamber) 51 in which the liquid matter is filled, a reservoir 53, and an orifice (supply port) 52 for allowing mutual communication between the reservoir 53 and the cavity 51 are provided. At the portion of the nozzle plate 41 corresponding to the cavity 51, a nozzle (exit) 16 for allowing communication between the inside and outside of the cavity is provided. The portion of the silicon substrate 42 facing the cavity 51 is formed in a vibrating plate (bottom wall) 45 having a thickness thinner than other portions.

The vibrating plate 45 is arranged so as to elastically deform (elastically displace) in the outward direction of the surfaces (thickness direction), i.e., in the vertical direction.

The vibrating plate 45, a segment electrode 46 disposed on the upper part of the glass substrate 43, and an insulative layer 47 and an air gap (concave portion) 54 between them constitute the main part of the electrostatic type actuator (actuator) 44.

A discharge head drive circuit (voltage applying means) 29 including a drive circuit for applying a drive voltage between the segment electrodes 46 and common electrode 48 opposite to the segment electrodes 46 (between opposed electrodes) performs charge and discharge between the respective opposed electrodes in response to signals (discharge data) input from a CPU 28, which will be described later. One output terminal of the discharge head drive circuit 29 is connected to the respective segment electrodes 46 and the other output terminal is connected to an input terminal 49 of the common electrode 48 formed on the silicon substrate 42. Note that, since the silicon substrate 42 is doped with an impurity and the impurity itself has conductivity, a voltage can be applied (supplied) from the input terminal 49 to the vibrating plate 45 (entire common electrode 48).

When a drive voltage is applied between the opposed electrodes from the discharge head drive circuit 29, a coulomb force is generated between the opposed electrodes and the vibrating plate 45 is bowed toward the segment electrode 46 relative to the initial state shown in FIG. 4, and the volume of the cavity 51 increases (expands). In this state, when the electric charge between the opposed electrodes is drastically discharged by the control of the discharge head drive circuit 29, the vibrating plate 45 is restored upwards by its elastic restoration force and moves upwards over the position of the vibrating plate 45 in the initial state shown in FIG. 4, and the volume of the cavity 51 drastically decreases (contracts). Thereby, the pressure within the cavity 51 increases and, by the compression pressure generated within the cavity 51, a part of the liquid matter filling up the cavity 51 is discharged as droplets from the nozzles 16 communicating with the cavity 51.

Further, at the portion of the glass substrate 43 corresponding to the reservoir 53, an intake port 55 communicating with the reservoir 53 is provided. To the intake port 55, the base end side of a supply pipe 33, which will be described later, is coupled, and the liquid matter is supplied into the reservoir 53 from a cartridge 21, which will be described later, via the supply pipe 33 and the intake port 55.

The atomizing means 18 in the embodiment is constituted by heating means for receiving and heating the droplets of the liquid matter discharged from the nozzles 16 of the respective discharge heads 15 to atomize them.

That is, as shown in FIG. 3, the atomizing means 18 has a droplet receiving plate (droplet receiving part) 181 for receiving the droplets of the liquid matter discharged from the nozzles 16 of the respective discharge heads 15 and a heating part 182 provided below the droplet receiving plate 181 in the drawing for heating the droplet receiving plate 181. The atomizing means 18 heats the droplet receiving plate 181 by the heating part 182 to atomize the droplets received by the droplet receiving plate 181. Alternatively, the droplet receiving plate 181 and the heating part 182 may be integrally constituted.

In this case, the average particle diameter of the atomized liquid matter is preferably on the order of 1 to 100 μm, and, in the case where the liquid matter is deposited before reaching the back of the throat, 10 μm or more is preferable. Further, in the case where the liquid matter is allowed to reach the larynx at the back of the throat, the bronchi, and the lungs, 10 μm or less is preferable.

The droplet receiving plate 181 is opposed to the nozzles 16 (nozzle surface) of the respective discharge heads 15 and disposed by being spaced at a predetermined distance from the tip ends of the nozzles 16 (nozzle surface). The spaced distance L is preferably on the order of $D \cdot Vd/Va \pm (D \cdot Vd/Va)/5$ in order to improve the probability of landing, assuming that the maximum wind velocity obtained from the intake airflow is Va, the droplet velocity is Vd, and the length of the droplet receiving plate 181 in the airflow direction is D, and more preferably on the order of $(D \cdot Vd/Va)/2 \pm (D \cdot Vd/Va)/10$. The respective dimensions (units) are expressed in unified units such as (mm) in order to represent the mutual ratio.

The space between the nozzles 16 (nozzle surface) of the respective discharge heads 15 and the droplet receiving plate 181 is the above described channel 3 for allowing communication of air etc., and, by the air circulating in the channel 3, the atomized (nebulized) liquid matter flows. That is, the atomized liquid matter is mixed with the air circulating within the channel 3 into mixed gas, flows within the channel 3, and is released from the aspiration opening 4 to be inhaled by the user.

As the heating part 182, not limited as long as one has a function of heating the droplet receiving plate 181, for example, a micro-heater and the like can be cited. The micro-heater is for converting the electricity into thermal energy, and its form and system can be arbitrarily selected. Normally, a heater thin film is formed and heat is generated by allowing current to flow in its resistance.

By the way, a part or the entire (whole) atomizing means 18 may be arranged so as to be detachably mounted to the casing 2 (apparatus main body 100).

That is, for example, only the droplet receiving plate 181, or both the droplet receiving plate 181 and the heating part 182 may be arranged so as to be detachably mounted to the casing 2.

Thereby, the receiving face (surface) for receiving the droplets in the droplet receiving plate 181 can be easily cleaned.

Further, a part or the entire (whole) atomizing means 18 is provided to the cartridge 21 (the cartridge 21 and a part or the entire (whole) atomizing means 18 are integrated), these may be integrally arranged so as to be detachably mounted to a cartridge chamber (mounted portion) 8 of the casing 2 (apparatus main body 100).

As shown in FIG. 2, in the middle of the channel 3 (the basal portion of the tapered surface 5 of the channel 3) on the leading end side (the left side in the drawing) of the discharging means 14 (atomizing means 18), an air flow sensor 19 as detection means is provided, and, by the air flow sensor 19, the flow rate of the fluid (air or mixed gas of air and a predetermined component) circulating within the channel 3 is detected.

By the way, the air flow sensor 19 may be provided on the downstream side of the discharging means (atomizing means 18), i.e., on the base end side (the right side in FIG. 2).

Further, in the middle of the channel 3 on the base end side (the right side in the drawing) of the discharging means 14 (atomizing means 18), heating means 20 is provided, and, by the activation of the heating means 20 according to the need because of the property of the medical agent and the like, the fluid (air or mixed gas of air and a predetermined component) circulating within the channel 3 is heated, and the fluid heated at predetermined temperature flows out from the aspiration opening 4. As the heating means 20, not limited as long as one has a function of heating the fluid, for example, a micro-heater etc. can be cited.

Note that the heating means 20 is made detachable from the mouth piece 7, for example, and may be mounted to the mouth piece 7 according to the need.

Further, the heating means 20 may be provided on the upstream side of the discharging means 14 (atomizing means 18), i.e., on the leading end side (the left side in FIG. 2), and arranged so as to heat the air before circulating within the channel 3 and reaching the discharging means 14 (the air before being mixed with the droplets of the liquid matter) by the activation of the heating means 20.

Further, at the center of the casing 2 in the longitudinal direction (the portion of the channel 3 on the left side in the drawing), the cartridge chamber (mounted portion) 8 in a predetermined depth having the upper surface open to the outer surface side of the casing 2 is provided, and, within the cartridge chamber 8, the cartridge 21 stored (filled) with the liquid matter is detachably mounted. On one end surface (the left side in FIG. 2) of the cartridge chamber 8 in the axial direction, a cartridge detection-power switch 9 is provided. When the cartridge 21 is mounted (attached) in the cartridge chamber 8, the cartridge detection-power switch 9 is turned ON and the mounted state of the cartridge 21 is detected, and the power supply 26 is turned ON. When the cartridge 21 is removed (detached) from the cartridge chamber 8, the cartridge detection-power switch 9 is turned OFF and the demounted state of the cartridge 21 is detected, and the power supply 26 is turned OFF.

The cartridge 21 has a cartridge main body (casing) 210 having an overall form of box shape. Within a chamber 212 inside the cartridge main body 210, a predetermined amount of the liquid matter is stored (filled).

The construction material of the cartridge main body (casing) 210 is not limited, but, for example, various resins etc. can be cited.

By the way, a part or the entire (whole) above described discharging means 14 is provided to the cartridge 21 (the cartridge 21 and a part or the entire (whole) of the discharging means 14 are integrated), these may be integrally arranged so as to be detachably mounted to the cartridge chamber (mounted portion) 8 of the casing 2 (apparatus main body 100).

On the lower surface side of the chamber 212 of the cartridge main body 210, a pierced portion 211 in which a sharp end portion 331 on the leading end side of the supply pipe 33, which will be described later, is pierced is formed. When the cartridge 21 is mounted in the cartridge chamber 8, the sharp end portion 331 of the supply pipe 33 pierces and penetrates the pierced portion 211 of the cartridge main body 210. Thereby, the inside of the chamber 212 and the supply pipe 33 are communicably connected.

On the outer periphery of the casing 2, the supply pipe 33 allowing mutual communication between the part of the cartridge chamber 8 corresponding to the chamber 212 and the above described discharging means 14 in the axial direction is buried. At the leading end of the supply pipe 33, the sharp end portion (piercing needle) 331 is formed. The liquid matter is supplied from the chamber 212 of the cartridge 21 to the discharging means 14 via the supply pipe 33.

Further, at the leading end of the casing 2 (part of the cartridge chamber 8 on the left side in the drawing), the power supply (power supply part) 26 is built in on the base end side, and control means 27 for controlling the drive of the discharging means 14, the atomizing means 18, the airflow sensor 19, the heating means 20, the power supply 26, etc. is built in on the leading end side thereof, respectively. By the way, the power supply 26 is arranged so as to be detachably mounted within the casing 2.

As the power supply 26, for example, a battery such as a primary cell and a secondary cell can be used. In this case, by using a fuel cell having high energy density, miniaturization and weight reduction can be ensured. The fuel cell may be formed in a cartridge form for easy replacement.

Further, at the leading end portion 11 (the other end in the longitudinal direction) of the casing 2, a ring (ring body) 12 is provided rotatably and movably. To the ring 12, for example, a cord, chain or the like (not shown) is attached and placed around the user, and thereby, the electronic inhalator apparatus 1 can be dangled from the neck like an accessory (necklace). This makes carrying of the electronic inhalator apparatus 1 very convenient, and the user can use it at any time anywhere easily and rapidly when the user wants to use the electronic inhalator apparatus 1.

As shown in FIG. 5, the control means 27 includes the CPU (Central Processing Unit) 28 for controlling the drive of the discharging means 14, the atomizing means 18, the heating means 20, the airflow sensor 19, the power supply 26, etc., the discharge head drive circuit 29 in which a circuit for driving the discharging means 14 is incorporated, and an atomizing means drive circuit 30 in which a circuit for driving the atomizing means 18.

The electronic inhalator apparatus 1 (atomizing device 10) according to the embodiment can perform various kinds of control by having the control means 27 described above.

For example, in the case where the electronic inhalator apparatus 1 is applied to the apparatus for inhalation of a medical agent (medical component), by the control means 27, the released amount (inhaled amount) of the medical agent (medical component), i.e., the total amount of the medical component passing through the aspiration opening 4 is regulated (controlled), and thereby, the dosage of the medical agent can be controlled. Therefore, the main function of the regulating means for regulating the total amount of the predetermined component passing through the aspiration opening 4 (release opening) is achieved by the control means 27.

The regulation of the total amount of the medical component passing through the aspiration opening 4 can be performed by regulating the total amount of the droplets discharged from the discharging means 14.

Further, the heating of the air or the mixed gas of the air and the predetermined component by the heating means 20 can be controlled to be turned ON because the improvement in the immediate results of the medical agent and secondary produced medical agent by thermal decomposition are desired. Furthermore, for example, in the case where the medical agent is inhaled, ON/OFF of the heating means 20 can be switched according to the kind of the medical agent and the like.

When the user puts the mouth piece 7 of the electronic inhalator apparatus 1 (atomizing device 10) according to the embodiment arranged as described above to the user's lips (puts it in the mouth) and breaths in, the air flows from the intake opening 6 into the channel 3, the airflow circulating within the channel 3 is detected by the airflow sensor 19, the discharging means 14 is driven by the control means 27 according to the signal from the airflow sensor 19 (based on the detection result of the airflow sensor 19), the droplets of the predetermined amount of the liquid matter are discharged from the nozzles 16 of the discharge heads 15 into the channel 3. The droplets are atomized by the atomizing means 18, the air circulating within the channel 3 and the atomized liquid matter (predetermined component) are mixed, and the mixed gas thereof flows from the aspiration opening 4 into the mouth.

For example, in the case where the predetermined component is a flavor component, the flavor component is diffused within the mouth and the flavor component can be tasted.

Further, in the case where the predetermined component is a medical component, the medical flavor component can be inhaled (aspired).

In this case, since the fluid jet system (for example, inkjet system) is adopted for the discharging means 14, the target amount of droplets can be discharged from the discharging means 14 accurately and reliably. Thereby, the predetermined component can be aspired accurately and reliably to the target amount.

Further, a sufficient amount of droplets can be discharged into the casing 2 from the start of driving of the discharging means 14 and a sufficient amount of predetermined component can be aspired from the start of aspiration.

Furthermore, miniaturization, weight reduction, energy conservation, stable atomization, and uniform diameter and miniaturization of the liquid matter can be ensured.

Next, the second embodiment will be described.

Figure 6:
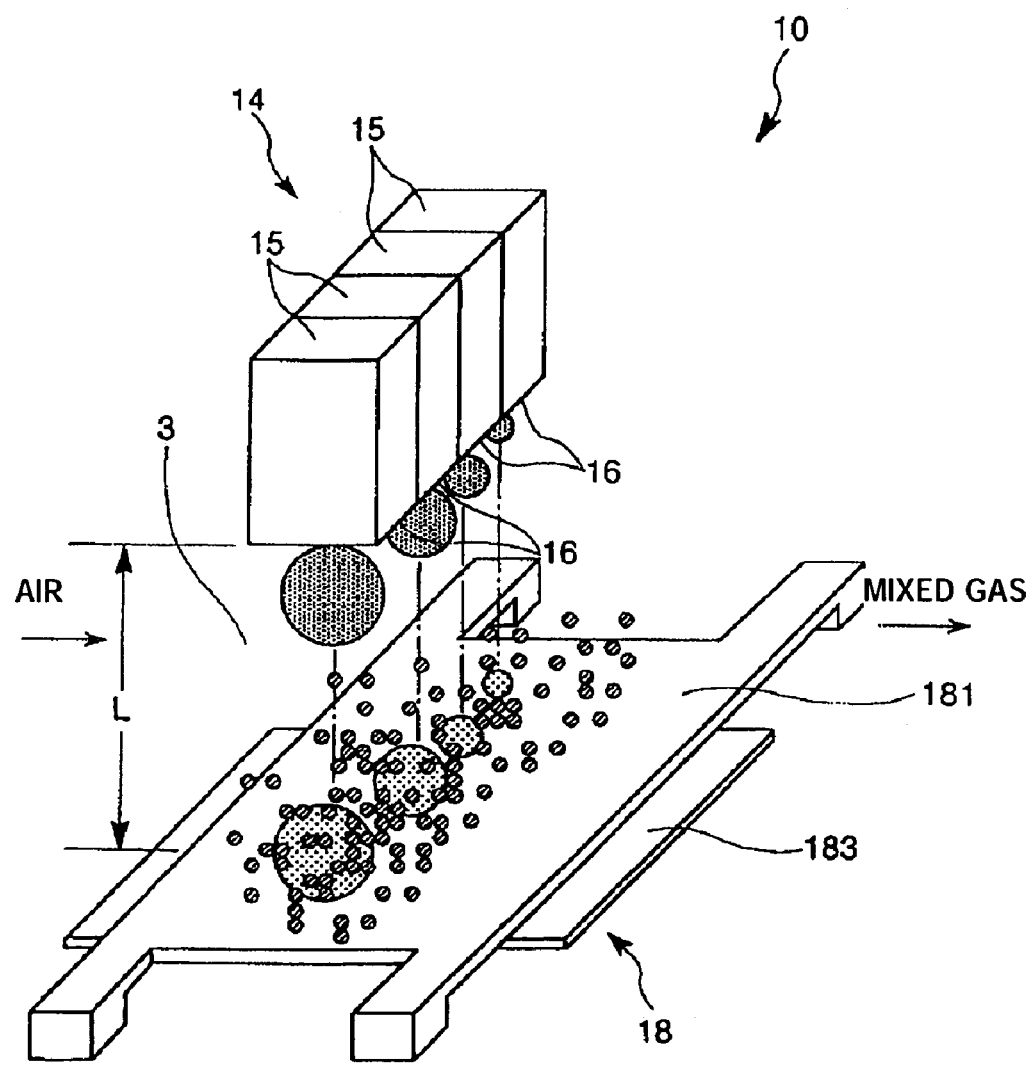
FIG. 6 is a view schematically showing a constitution example of discharge means and atomizing means in the second embodiment of the atomizing device of the invention.

FIG. 6 schematically shows an example of discharge means and atomizing means in the second embodiment of the atomizing device of the invention.

As described below, the atomizing device 10 of the second embodiment will be described with a focus on the point different from the above described first embodiment, and the description of the same parts will be omitted.

In the atomizing device 10 of the second embodiment, the atomizing means 18 is constituted by vibrating means for receiving and vibrating the droplets of the liquid matter discharged from the nozzles 16 of the respective discharge heads 15 to atomize them.

That is, as shown in FIG. 6, the atomizing means 18 has a droplet receiving plate (droplet receiving part) 181 for receiving the droplets of the liquid matter discharged from the nozzles 16 of the respective discharge heads 15 and a vibrating part 183 provided below the droplet receiving plate 181 in the drawing for vibrating the droplet receiving plate 181. The atomizing means 18 vibrates the droplet receiving plate 181 by the vibrating part 183 to atomize the droplets received by the droplet receiving plate 181.

As the vibrating part 183, not limited as long as one has a function of vibrating the droplet receiving plate 181, for example, an ultrasonic vibration generating unit and the like can be cited. Further, the droplet receiving plate 181 and the vibrating part 183 may be constituted integrally.

Since the remaining elements are the same as that shown in the first embodiment, the description thereof will be omitted.

According to the atomizing device 10, the same advantage as that in the first embodiment can be obtained.

As described above, the invention is described according to the shown embodiments, however, the invention is not limited thereto, and the constitution of each part can be replaced by an arbitrary constitution having an equivalent function. Further, other arbitrary constitution can be added to the invention.

In addition, in the invention, blower means for blowing (sending) air circulating within the casing or the mixed gas including the air and the predetermined component may be provided.

Further, in the above described embodiments, the case where the atomizing device is applied to the electronic inhalator apparatus is described as an example, however, the application of the atomizing device of the invention is not limited to that, but the device can be applied to others, for example, various kinds of electronic equipment including a device for atomizing (nebulizing) the liquid matter such as an electronic tobacco (pseudo-smoking instrument). In addition, the atomizing device of the invention may be used by providing it at the outlet of an air conditioner.

What is claimed is:

1. An atomizing device comprising:

a casing having a leading end portion, a release opening disposed on an opposite end of said casing from said leading end portion, an air inlet opening, and a tapered surface extending between said air inlet opening and said release opening, said air inlet opening being substantially perpendicular to a longitudinal axis of said casing and extending between said release opening and said leading end portion;

discharging means provided within said releasing opening of said casing and having at least one discharge head for discharging a liquid matter as droplets from a nozzle communicating with a cavity defined between said air inlet opening and said release opening by driving an actuator to change pressure within said cavity filled with said liquid matter;

atomizing means provided within said casing for atomizing the droplets discharged from said discharging means;

a storage cartridge disposed along said longitudinal axis for storing said liquid matter, said storage cartridge including a pierced portion for piercing said storage cartridge and communicating said liquid matter to said discharging means through a supply pipe formed in said casing;

a control means disposed along said longitudinal axis for controlling said discharging means and said atomizing means; and a power supply disposed along said longitudinal axis between said control means and said storage cartridge for supplying power to said discharge means and said atomizing means;

wherein said atomized droplets of liquid matter are mixed with inlet air from said inlet air opening and are directed toward said release opening by said tapered surface within said cavity prior to said mixture of inlet air and atomized droplets being discharged from said release opening.

2. The atomizing device according to claim 1, wherein at least one of:

at least a part of said discharging means; and at least a part of said atomizing means;

is detachably mounted to said casing.

3. The atomizing device according to claim 1, wherein said atomizing means comprises vibrating means for vibrating and atomizing the droplets discharged from said discharging means.

4. The atomizing device according to claim 1, wherein said atomizing means has a droplet receiving part spaced at a predetermined distance from said nozzle for receiving said droplets.

5. The atomizing device according to claim 4, wherein said atomizing means atomizes the droplets received by the droplet receiving part by vibrating said droplet receiving part.

6. The atomizing device according to claim 1, wherein said casing includes a first diameter at said air inlet opening and a second diameter at said release opening, said second diameter being smaller than said first diameter and cooperating with said tapered surface to direct said atomized droplets of liquid matter and said inlet air toward said release opening.

7. The atomizing device according to claim 1, wherein said cartridge is detachably mounted to said casing.

8. The atomizing device according to claim 7, wherein at least one of:

at least a part of said discharging means; and at least a part of said atomizing means;

is mounted to said storage cartridge such that said storage cartridge is disposed along said longitudinal axis between said cavity and said power source.

9. The atomizing device according to claim 7, further comprising a power switch for selectively turning said power supply ON and OFF by attaching said cartridge to and detaching it from said casing.

10. The atomizing device according to claim 1, wherein said liquid matter includes a component taken in by a living body.

* * * * *